United States Patent [19]

Bellus et al.

[11] 4,013,445
[45] Mar. 22, 1977

[54] 1-(BIS-TRIFLUOROMETHYLPHENYL)-2-OXO-PYRROLIDINE-4-CARBOXYLIC ACID DERIVATIVES, THEIR PRODUCTION AND THEIR USE AS PLANT-GROWTH REGULATORS AND HERBICIDES

[75] Inventors: Daniel Bellus, Riehen; Werner Fory, Basel, both of Switzerland

[73] Assignee: Ciba-Geigy Corporation, Ardsley, N.Y.

[22] Filed: Oct. 23, 1975

[21] Appl. No.: 625,234

[30] Foreign Application Priority Data

Oct. 31, 1974 Switzerland .................. 14595/74

[52] U.S. Cl. .................................... 71/76; 71/78;
71/95; 260/326.5 J; 260/326.5 R; 260/268 H; 260/293.71; 260/326.45

[51] Int. Cl.² ................................... A01N 9/28

[58] Field of Search .............. 260/326.45, 326.5 J, 260/326.5 R, 268 H, 293.71; 71/95

[56] References Cited

UNITED STATES PATENTS 3,149,954   9/1964   Harrod .................. 260/326.45

*Primary Examiner*—Lewis Gotts
*Assistant Examiner*—Cary Owens
*Attorney, Agent, or Firm*—Harry Falber

[57] ABSTRACT

The present invention relates to new 1-(bis-trifluoromethylphenyl)-2-oxo-pyrrolidine-4-carboxylic acid derivatives, to processes for their production, to compositions containing these active substances, as well as to the use of these active substances and compositions for the regulation of plant growth and as herbicides.

These derivatives correspond to formula I

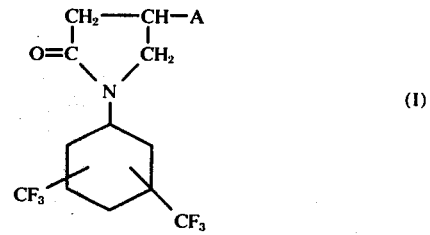

wherein A represents the nitrile or carboxylic acid group or a derivative of the carboxylic acid.

8 Claims, No Drawings

1-(BIS-TRIFLUOROMETHYLPHENYL)-2-OXO-PYRROLIDINE-4-CARBOXYLIC ACID DERIVATIVES, THEIR PRODUCTION AND THEIR USE AS PLANT-GROWTH REGULATORS AND HERBICIDES

The present invention relates to new 1-(bis-trifluoromethylphenyl)-2-pyrrolidine-4-carboxylic acid derivatives, to processes for their production, to compositions containing these active substances, as well as to the use of these active substances and compositions for the regulation of plant growth and as herbicides.

The use of 1-phenyl-2-oxo-pyrrolidine-4-carboxylic acids, and derivatives thereof, which are unsubstituted on the phenyl nucleus or substituted thereon by halogen atoms and/or a trifluoromethyl group, as active substances for the regulation of plant growth, is known from the French Patent Specification No. 1,363,615 and from the U.S. Patent No. 3,136,620. The action of these prior known compounds, such as 1-(3-trifluoromethyl-4-chlorophenyl)-2-oxo-pyrrolidine-4-carboxylic acid and 1-(3,4-dichlorophenyl)-2-oxo-pyrrolidine-4-carboxylic acid, is however inadequate. Furthermore, these hitherto known compounds are in some cases phytotoxic in the usual amounts applied.

It has now been found that compounds of the formula I

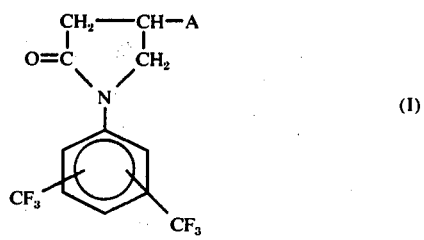

wherein A represents a group $-COO^- H^+$, $-COOR_1$, $-COSR_2$, $-CN$, $-COCl$, $-COF$, $-CO\text{-}O\text{-}CO\text{-}R_3$, $-COO\text{-}Si(CH_3)_3$,

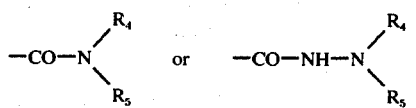

$R_1$ represents the equivalent of a mono- to trivalent metal cation or of an inorganic or organic amine cation or quaternary ammonium cation, also an unsubstituted or substituted $C_1$–$C_{18}$-alkyl radical, an alkenyl, halogenoalkenyl, alkynyl or halogenoalkynyl radical having 3 to 8 carbon atoms, a cycloalkyl radical having 3 to 12 ring carbon atoms, optinally substituted phenyl, benzyl or phenethyl, $R_2$ represents an alkyl radical having 1 to 6 carbon atoms or an optionally substituted phenyl or benzyl radical, $R_3$ represents a $C_1$–$C_4$-alkyl radical optionally substituted by at most 3 halogen atoms, or phenyl, $R_4$ and $R_5$ each independently represent hydrogen, optionally substituted alkyl having 1-6 carbon atoms in the chain, $C_3$–$C_8$-alkenyl, cycloalkyl having 3 to 8 ring carbon atoms, optionally substituted phenyl, or $R_4'$ and $R_5$ together with the adjacent nitrogen atom also represent an optionally substituted, saturated 3- to 8-membered heterocyclic ring, which can also contain a further hetero atom, have a substantially better and more flexible sphere of action than that of the prior known compounds.

Alkyl groups denoted by the various symbols $R_1$ to $R_5$ can be straight-chain or branched-chain.

Alkyl groups $R_1$, $R_4$ and $R_5$ can contain as substituents, for example, 1-3 halogen atoms, especially fluorine, chlorine or bromine atoms, hydroxyl, alkoxy, alkylthio, amino, mono- or dialkyl-substituted amino groups, or a cyano, alkoxycarbonyl, carbamoyl, tetrahydrofuryl, tetrahydropyranyl or oxacyclopropyl group, with the alkyl moieties in these substituents having 1-4, particularly 1 or 2, carbon atoms.

Substituents of phenyl, benzyl or phenylethyl groups denoted by $R_1$, $R_2$, $R_4$ or $R_5$ are, e.g., alkyl, alkoxy, alkylthio, N-alkylamino or N,N-dialkylamino groups each having 1-4 carbon atoms in the alkyl or alkoxy moieties, halogen atoms, particularly chlorine or fluorine, trifluoromethyl, amino and nitro groups.

Halogen substituents on alkenyl or alkynyl groups $R_1$ and on alkyl groups $R_3$ are, e.g., bromine, especially however fluorine or chlorine.

If $R_4$ and $R_5$ together with the nitrogen atom to which they are bound form a substituted heterocyclic ring, such as piperidine, piperazine or morpholine, then substituents are, in paticular, alkyl groups having 1–4 carbon atoms.

Preferred compounds of the formula I are those wherein the two trifluoromethyl groups are in the 3- and 5-position of the phenyl group.

The symbol A represents preferably one of the following groups:

—COOH;

-COOR$_1$ wherein R$_1$ represents unsubstituted alkyl having 1–6 carbon atoms, especially methyl, or benzyl;

—COSR$_2$ where R$_2$ denotes alkyl having 1-4 carbon atoms.

Further preferred compounds of the formula I are those wherein $R_1$ represents an alkali metal cation, particularly the sodium or potassium cation, or the cation of an organic amine.

Suitable metal cations $R_1$ are also those of alkaline-earth metals, of zinc, copper or iron. If the cation present is bi- or trivalent, then it is naturally combined with the number of anions of the parent carboxylic acid of the formula I (A = COO $^-$) corresponding to its valency. Thus 1/n cation having the valency n corresponds to the parent compound I. The compounds of the formula I according to the invention can be produced in a manner known per se by a process wherein an aniline of the formula II

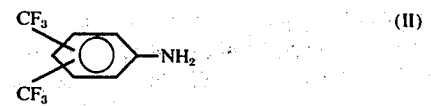

is reacted with itaconic acid to a compound of the formula I wherein A represents the carboxyl group, and the 1-(bis-trifluoromethylphenyl)-2-oxo-pyrrolidine-4-carboxylic acid obtained is optionally converted into another derivative as defined.

The anilines of the formula II are known per se and can be produced in a conventional manner.

The reaction of the anilines of the formula II with itconic acid can be performed in the melt or in an aqueous, aqueous-organic or organic medium.

Employed organic solvents can be, e.g., aliphatic alcohols such as methanol and ethanol, cyclic ethers such as dioxane, aromatic hydrocarbons such as benzene and toluene, or sulpholane, pyridine and pyridine bases.

The reaction temperatures are in general between 100° and 250° C.

The conversion of the 1-(bis-trifluoromethylphenyl)-2-oxo-pyrrolidine-4-carboxylic acids into other derivatives of the formula I as defined is carried out likewise in a manner known per se; for example
ester ($A = COOR_1$) by reaction of the free carboxylic acids with alkyl halides $R_1$-Hal in the presence of a base; by reaction of the free carboxylic acids, or of the corresponding acid chlorides or acid fluorides, with alcohols $R_1OH$; or by transesterification;
acid chlorides and fluorides ($A = $ -COCl, -COF) by reaction of the free carboxylic acids with suitable chlorinating or fluorinating agents, such as thionyl chloride, oxalyl chloride, phosgene, $PCl_5$ or sulphur tetrafluoride ($SF_4$);

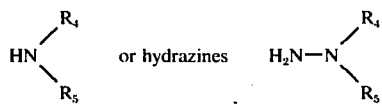

by reaction of the free acids, acid esters, acid chlorides or acid fluorides with amines

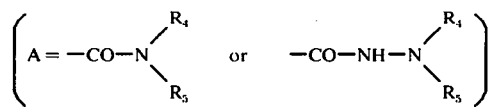

nitriles ($A = $ -CN) by dehydration of the acid amides in the presence of suitable dehydrating agents, such as $P_2O_5$ or $SOCl_2$;
thioesters ($A = $ -$COSR_2$) by reaction of the acid chlorides or acid fluorides with mercaptans $HSR_2$;
mixed anhydrides ($A = $ -CO-O-CO-$R_3$) by reaction of the free carboxylic acids, or their salts, acid chlorides or fluorides, with anhydrides ($R_3$-CO)$_2$-O;
siloxanes [$A = $ —COO-Si(CH$_3$)$_3$] by reaction of the free carboxylic acids with suitable silylating agents, such as bis-(trimethylsilyl)-acetamide, trimethylchlorosilane and bis-(trimethyl)-silazane;
alkali metal salts, alkaline-earth metal salts, Zn-, Cu- and Fe-salts
by reaction of the free carboxylic acids with alkali metal hydroxides or alkaline-earth metal hydroxides, alkali metal alcoholates or alkaline-earth metal alcoholates or alkali metal carbonates, or alkaline-earth metal carbonates, such as Na-, K-, Li-, Ca- and Mg-hydroxide, sodium methylate and potassium methylate and sodium ethylate and potassium ethylate, and reaction of these alkali metal salts, particularly sodium salts, with inorganic, water-soluble zinc, copper and iron salts;
ammonium salts and amine salts
by reaction of the free carboxylic acid with ammonia, $NH_2$-$NH_2$, amines having 1 to 2 nitrogen atoms which are separated by straight or cyclic alkylene bridges, or with corresponding quaternary ammonium bases of the type $N^{+-}(R)_4$-$OH^-$ or $(R)_3N^+$-R-$N^+(R)_3$ $(OH)_2^-$ in a molar ratio of 1:1 or 2:1.

Esters of formula I ($A = $ -$COOR_1$) can be obtained according to a modified process also by reaction of an aniline of the formula II with an itaconic acid diester of the formula III

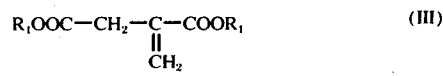

wherein $R_1$ has the above-given meaning.

The reaction of the anilines of the formula II with the itaconic acid diesters is advantageously performed in the melt, or in an inert organic solvent, e.g., aliphatic alcohols, at a temperature of between 100° and 250° C.

After completion of the reaction, the compounds of the formual I are isolated and purified in the usual manner, e.g. by dissolving and reprecipitating, or by filtration and recrystallisation from suitable solvents such as diethyl ether, n-hexane or aliphatic alcohols having 1–4 carbon atoms.

The following Examples illustrate the production of some compounds of the invention.

EXAMPLE 1

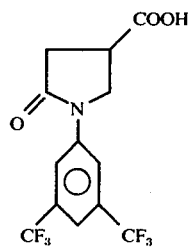

229 g (1 mole) of 3,5-bis-(trifluoromethyl)-aniline and 136.5 g (1.05 moles) of itaconic acid are stirred in 55 ml of water during 24 hours at 200° C in an autoclave. The reaction mixture is subsequently cooled to 20° C and 2 liters of cold water are added. Two liters of water are then evaporated, and the reaction mixture is again cooled to 20° C. The crystals that have precipitated are filtered off, dried, dissolved in 400 ml of diethyl ether and precipitated with 600 ml of n-hexane. There is obtained 242 g (71% of theory) of 1-(3,5-bis-trifluoromethylphenyl)-2-oxo-pyrrolidine-4-carboxylic acid; m.p. 108°–9° C.

Analysis for $C_{13}H_9F_6NO_3$ (molar weight 341.22):

| | | | | | | | |
|---|---|---|---|---|---|---|---|
| calculated: | C | 45.79% | H | 2.67% | F | 33.42% | N | 4.11% |
| found: | C | 45.77% | H | 2.79% | F | 32.91% | N | 4.09% |

EXAMPLE 2

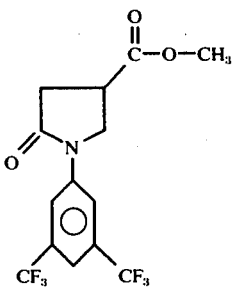

8.8 g (0.025 mole) of the 1-(3,5-bis-trifluoromethylphenyl)-2-oxo-pyrrolidine-4-carboxylic acid produced according to Example 1 is refluxed together with 0.3 g of p-toluenesulphonic acid in 130 ml of absolute methanol, and the reaction mixture is kept at this temperature during 17 hours. It is subsequently cooled to 20° C and 0.1 g of sodium carbonate is added. Excess methanol is evaporated off. The residue is dissolved in diethyl ether, extracted three times with water, dried, and concentrated by evaporation. By recrystallisation from n-hexane there is obtained 8.4 g (91% of theory) of 1-(3,5-bis-trifluoromethylphenyl)-2-oxo-pyrrolidine-4-carboxylic acid methyl ester; m.p. 68°–70° C. Analysis for $C_{14}H_{11}F_6NO_3$ (molar weight 355.17):

| calculated: | C 47.30% | H 3.12% | F 32.10% | N 3.97% |
|---|---|---|---|---|
| found: | C 47.42% | H 3.17% | F 31.97% | N 4.08% |

EXAMPLE 3

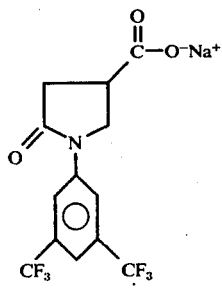

1.62 g (0.03 mole) of sodium methylate is added at 20°–25° C to a solution of 10.24 g (0.03 mole) of the 1-(3,5-bis-trifluoromethylphenyl)-2-oxo-pyrrolidine-4-carboxylic acid, produced according to Example 1, in 50 ml of absolute methanol. The reaction is completed after 10 minutes. After removal of the methanol by evaporation, there is obtained 10.9 g (100% of theory) of the sodium salt of 1-(3,5-bis-trifluoromethylphenyl)-2-oxo-pyrrolidine-4-carboxylic acid in the form of a white powder; m.p.>310° C. Analysis for $C_{13}H_8F_6NNaO_3$ (molar weight 363.20).

| calculated: | C 42.98% | H 2.22% | F 31.38% | N 3.86% | Na 6.33% |
|---|---|---|---|---|---|
| found: | C 42.38% | H 2.28% | F 30.90% | N 3.44% | Na 6.60% |

EXAMPLE 4

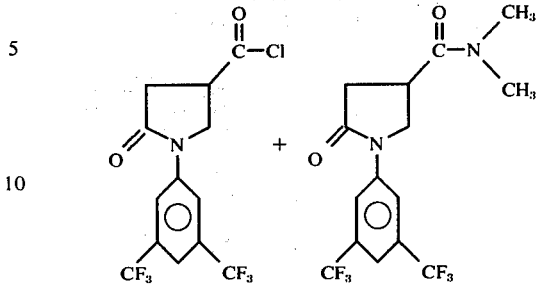

43 g (0.126 mole) of 1-(3,5-bis-trifluoromethylphenyl)-2-oxo-pyrrolidine-4-carboxylic acid, produced according to Example 1, and 22.5 g (0.19 mole) of thionyl chloride are suspended in 135 ml of benzene, and the reaction mixture is refluxed for 18 hours. A clear solution is formed and is subsequently concentrated by evaporation. By distillation of the residue at 160° C/0.004 Torr, there is obtained 1-(3,5-bis-trifluoromethylphenyl)-2-oxo-pyrrolidine-4-carboxylic acid chloride in a 90% yield.

40.6 g (0.113 mole) of the acid chloride produced in this manner is dissolved in 400 ml of benzene. The reaction solution obtained is treated at 0° C with gaseous N,N-dimethylamine.

The resulting precipitate is filtered off, repeatedly washed with water, dried, and recrystallized from a mixture of diethyl ether and n-hexane (volume ratio 40:60). There is obtained 26.4 g (63.5% of theory) of 1-(3,5-bis-trifluoromethylphenyl)-2-oxo-pyrrolidine-4-carboxylic acid-N,N-dimethylamide; m.p. 84.5°–86° C. Analysis for $C_{15}H_{14}F_6N_2O_2$ (molar weight 368.30):

| calculated: | C 48.91% | H 3.83% | F 30.95% | N 7.61% |
|---|---|---|---|---|
| found: | C 48.82% | H 3.82% | F 30.82% | N 7.78%. |

EXAMPLE 5

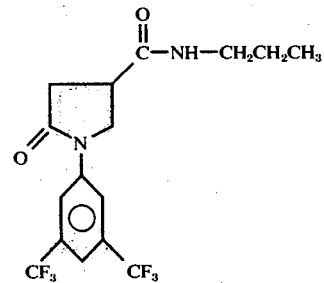

3.59 g (0.01 mole) of the 1-(3,5-bis-trifluoromethylphenyl)-2-oxo-pyrrolidine-4-carboxylic acid chloride, produced according to Example 4, paragraph 1, is dissolved in 400 ml of benzene, and 1.2 g (0.02 mole) of N-n-propylamine is added to the solution. After subsequent processing as described in Example 4 there is obtained 3.1 g (81% of theory) of 1-(3,5-bis-trifluoromethylphenyl)-2-oxo-pyrrolidine-4-carboxylic acid-N-n-propylamide; m.p. 152.5°–154° C. Analysis for $C_{16}H_{16}F_6N_2O_2$ (molar weight 382.32):

| calculated: | C 50.26% | H 4.22% | F 29.81% | N 7.32% |
|---|---|---|---|---|
| found: | C 49.85% | H 4.29% | F 28.85% | N 7.15%. |

EXAMPLE 6

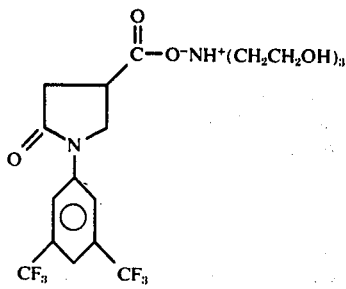

14.9 g (0.1 mole) of triethanolamine is added dropwise in the course of 15 minutes, with vigorous stirring, to a solution of 34.1 g (0.1 mole) of the 1-(3,5-bis-trifluoromethylphenyl)-2-oxo-pyrrolidine-4-carboxylic acid, produced according to Example 1, in 300 ml of diethyl ether. The solent is subsequently evaporated off to obtain 49 g (100% of theory) of the corresponding triethanolamine salt in the form of a white crystalline residue; m.p. 98°–101° C. Analysis for $C_{19}H_{24}F_6N_2O_6$ (molar weight 490.41):

| calculated: | C 46.49% | H 4.93% | F 23.20% | N 5.72% |
|---|---|---|---|---|
| found: | C 46.20% | H 5.10% | F 21.90% | N 5.80%. |

EXAMPLE 7

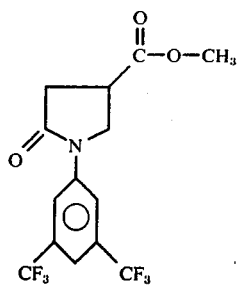

22.9 g (0.1 mole) of 3,5-bis-(trifluoromethyl)-aniline and 16.5 g (0.105 mole) of itaconic acid dimethyl ester are stirred for 48 hours at 200° C in an autoclave. The reaction mixture is subsequently cooled, and chromatographically separated through a silica gel column with a benzene/ethyl acetate mixture (volume ratio 85:15) as the eluant. The fractions containing 1-(3,5-bis-trifluoromethylphenyl)-2-oxo-pyrrolidine-4-carboxylic acid methyl ester are concentrated by evaporation, and recrystallised from n-hexane. There is obtained 4.3 g (12% of theory) of the above methyl ester; m.p. 68°–70° C.

EXAMPLES 8-70

Also the following compounds of the formula I are produced by the process of the invention:

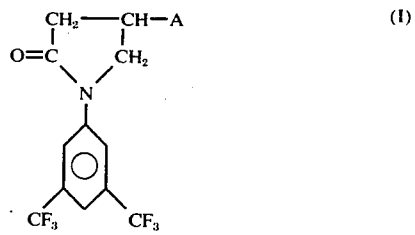

Table I

Compounds of the formula I

| Example No. | A | m.p. (° C) |
|---|---|---|
| 8 | —COO—(CH$_2$)$_7$—CH$_3$ | oil |
| 9 | —COO—(CH$_2$)$_{17}$—CH$_3$ | 49–50° |
| 10 | —COO—CH$_2$—CH=CH$_2$ | oil |
| 11 | —COO—CH$_2$—CH$_2$—C(H)(CH$_3$)—CH$_2$—CH$_2$—CH=C(CH$_3$)—CH$_3$ | oil |
| 12 | —COO—CH$_2$—C≡CH | 72–74° |
| 13 | —COO—CH$_2$—CH$_2$—C≡C—CH$_2$CH$_3$ | 64–66° |
| 14 | —COO—cyclopentyl | oil |
| 15 | —COO—cyclododecyl | 83–85° |
| 16 | —COO—CH$_2$CH$_2$Cl | oil |
| 17 | —COO—CH$_2$CH$_2$CH$_2$CH$_2$CH$_2$CH$_2$Cl | oil |
| 18 | —COO—CH$_2$CH$_2$OCH$_3$ | oil |
| 19 | —COO—CH$_2$CH$_2$OC$_4$H$_9$ | oil |
| 20 | —COO—CH$_2$CH$_2$SCH$_2$CH$_3$ | oil |
| 21 | —COO—CH$_2$CH$_2$CH$_2$N(CH$_3$)(CH$_3$) | |
| 22 | —COO—CH$_2$CH$_2$CN | 85–86° |

Table I-continued

Compounds of the formula I

| Example No. | A | m.p. (°C) |
|---|---|---|
| 23 | —COO—CH(COOC₂H₅)—CH₃ | oil |
| 24 | —COO—CH₂CCl₃ | oil |
| 25 | —COOCH₂CF₃ | |
| 26 | —COOCH₂—CH=C(Cl)—CH₃ | oil |
| 27 | —COO—C₆H₅ | 120–122° |
| 28 | —COO—(2-Cl,4-Cl-C₆H₃) | 125–127° |
| 29 | —COO—(3-NO₂-C₆H₄) | 79–80° |
| 30 | —COO—(4-N(CH₃)₂-C₆H₄) | 111–112° |
| 31 | —COO—CH₂—C₆H₅ | oil |
| 32 | —COO—CH₂—C₆H₄—OCH₃ | 88–90° |
| 33 | —COO—CH₂—CH₂—C₆H₅ | 90–91° |
| 34 | —COO—CH₂—(tetrahydrofuran-2-yl) | |
| 35 | —COO—CH₂—(tetrahydropyran-2-yl) | oil |
| 35a | —COO—CH₂—CH(—O—)CH₂ (glycidyl) | oil |
| 36 | —COS—n-C₄H₉ | $n_D^{20} = 1,4930$ |
| 37 | —COS—CH₂—C₆H₄—Cl | 58–62° |
| 38 | —COS—C₆H₅ | 91–93° |
| 39 | —CN | 143–146° |
| 40 | —CO—O—CO—CH₃ | |
| 41 | —CO—O—CO—CHCl₂ | |
| 42 | —COO—Si(CH₃)₃ | |
| 43 | —CO—NH—CH(CH₂CH₃)(CH₂CH₃) | 135–137° |
| 44 | —CO—NH—C(CN)(CH₃)(CH₃) | 158–160° |
| 45 | —CO—NH—CH₂CH₂CH₂OCH₃ | 130–132° |
| 46 | —CO—N(CH₂CH₂OH)(CH₂CH₂OH) | 88–90° |
| 47 | —CO—NH—CH₂CH₂CH₂N(CH₃)(CH₃) | 141–142° |
| 48 | —CO—NH—CH₂—CH=CH₂ | 152–154° |
| 49 | —CO—NH—(cyclopropyl) | 165–169° |

Table I-continued

Compounds of the formula I

| Example No. | A | m.p. (° C) |
|---|---|---|
| 50 | —CO—N(piperidine with CH₃) | $n_D^{20} = 1.5020$ |
| 51 | —CO—NH—(3,5-bis-CF₃-phenyl) | |
| 52 | —CO—NH₂ | 223° |
| 53 | —CO—NH—NH₂ | 280–283° |
| 53a | —CO—NH—CH₂—CH₂OH | 154–156° |
| 54 | —CO—NH—N(CH₃)₂ | 188° |
| 55 | —CO—NH—N(piperidine) | 139 |
| 56 | —CO—NH—N(N'-methylpiperazine) | 184° |
| 56a | —CO—N(aziridine) | 82° |

EXAMPLE 57:

1-(3,4-bis-trifluoromethylphenyl)-2-oxo-pyrrolidine-4-carboxylic acid

Table II

Compounds having cations $R_1$ (n = valency)

| Example No. | n | Cation $R_1$ | m.p. (° C) |
|---|---|---|---|
| 58 | 2 | $Cu^{++}$ | 260–264° |
| 59 | 2 | $Zn^{-+}$ | 134–136° |
| 60 | 1 | $N(n-C_4H_9)_4$ | oil |
| 61 | 1 | $\text{C}_6\text{H}_5\text{—CH}_2\text{—}\overset{+}{N}\text{—(CH}_3)_3$ | resin |
| 62 | 1 | $H_2\overset{+}{N}(CH_2CH_2OH)_2$ | 102° |
| 63 | 1 | $H_3\overset{+}{N}\text{—}n\text{-}C_{12}H_{25}$ | 89° |
| 64 | 1 | $\overset{+}{NH_4}$ | 123–125° |
| 65 | 1 | $H\overset{+}{N}(CH_3)(CH_2CH_2Cl)$ | |
| 66 | 2 | $H_3\overset{+}{N}\text{—}CH_2CH_2\text{—}\overset{+}{N}H_3$ | 164° |
| 67 | 2 | $H_3\overset{+}{N}\text{—(CH}_2)_6\text{—}\overset{+}{N}H_3$ | 203–205° |
| 68 | 2 | $H_3\overset{+}{N}\text{—(CH}_2)_{10}\text{—}\overset{+}{N}H_3$ | 184–186° |
| 69 | 2 | $(C_2H_5)_2\overset{+}{H}N\text{—}CH_2CH_2\text{—}N\overset{+}{H}(C_2H_5)_2$ | |
| 70 | 2 | $(CH_3)_2\overset{+}{H}N\text{—(CH}_2)_6\text{—}N\overset{+}{H}(CH_3)_2$ | 119° |

The active substances contained in the compositions of the invention influence the growth of plants in various ways. They thus inhibit, retard or prevent in the first place growth and germination. In the usual amounts applied, the compounds of the formula I are practically nonphytotoxic to the emerged plants, but they inhibit the growth in height in the case of various species of plants.

Compositions according to the invention which contain as active constituent at least one compound of the formula I are suitable, in particular, for the inhibition and control of plant growth on monocotyledonous and dicotyledonous plants, such as grasses, shurbs, trees, crops of cereals and leguminosae, sugar cane, tobacco, soya beans, onion and potato tubers, ornamental plants, fruit trees and grape vines.

By a process for inhibition of plant growth is meant a regulation of the natural development of the plant without changing the life cycle of the plant, determined by genetic properties, in the sense of a mutation. In the development of the plant (growth in height, formation of side shoots, new sprouting, blossom, fruit setting, etc.) there can be produced artificially retarding phases. The process of growth regulation is applied during the development of the plant at a point of time to be determined in the individual case. The active substances of the formula I can be applied before or after the emergence of the plants; for example directly to the seeds or to young seedlings, to roots, tubers, stems, leaves or flowers or to other parts of plants. This can be effected, e.g., by application to the plants of the active substance alone or of a composition containing the active substance, and/or by treatment therewith of the nutrient medium of the plant (soil).

The effect primarily achieved by the compounds of the formula I is the desired reduction of the size of the plant, especially of the growth in height. There is hence in general associated with this effect a certain modification of the form of the plant. As a direct consequence of the reduction of the growth in height there occurs a stengthening of the plant. Stronger leaves and petioles are formed. As a result of a shortening of the internode distances on monocotyledonous plants, the resistance to breaking or kinking is increased. As a result of these effects, crop losses due to thunder storms, continuous rain, etc., which normally lead to a flattening of crops of cereals and leguminosae, are largely prevented, and consequently the work of harvesting is made easier. A secondary effect is that the reduced growth in height of useful plants results in a saving of fertilisers. This applies to the same extent also to ornamental plants, ornamental lawns or sport fields or to other grassland areas.

One of the most difficult problems in connection with entirely grassed areas is however the cutting of the grass itself, whether it be grass in parks in residential districts, grass on industrial sites, on sport fields, along highways, on airfields, railway embankments or on embankments of waterways. In all these cases, a periodic cutting of the lawns or of the grass growing elsewhere is essential. This is very expensive in terms of labour and of machines, and, in addition, involves where road traffic is circulating considerable risks for the personnel concerned and for the road users. It is therefore precisely in areas with large traffic networks that there exists an urgent need on the one hand to maintain and cultivate the turf that is so necessary with regard to the consolidating of grass verges and embankments along public routes, and on the other hand to keep the grass by simple means at a moderate height during the entire vegetation period. This requirement is satisfied in a very favourable manner by application of active substances of the formula I according to the invention.

In an analogous manner, cutting work involving considerable labour costs can be reduced by the treatment of trees, shrubs and hedges, particularly in residential and industrial districts, with compounds of the formula I according to the invention.

Also the growth of shoots and/or the fruit-bearing capacity of fruit trees and grape vines can be advantageously influenced by the use of active substances of the formula I according to the invention.

Ornamental plants having a strong growth in height can be grown as compact pot plants by treatment with active substances of the invention.

The active substances of the formula I are applied also for inhibiting the growth of undesired side shoots, e.g. in the case of tobacco and ornamental plants, as a result of which the labour-intensive operation of pinching out these side shoots by hand is avoided; they are used also to inhibit the growth of side shoots on tubers in storage, for example in the case of ornamental-plant bulbs, onions and potatoes; and finally for increasing the yield of cultivated plants growing in an intensely vegetative form, such as soya beans and sugar cane, by accelerating, as a result of this application of active substances according to the invention, the transition from the vegetative phase to the generative phase, so that by reduction of the vegetative growth the generative growth is promoted.

Preferentially, the compound of the formula I according to the invention are used for inhibition of the growth in grasses and cereal crops, as well as for the favourable regulation of growth in the case of tobacco plants, soya bean plants and cultivated plants. Some of the new active substances also exhibit a fruit-abscission effect.

The new compostions may also be employed, however, for the control of weeds, in the pre-emergence or post-emergence process, in various cultivated crops, such as maize, rice, cotton, sorghum, lucerne, etc., particularly for the control of the weeds Avena fatua and Cyperus esculentus.

The amounts applied vary and are dependent on the point of time of application. They are in general between 0.1 and 5 kg of active substance per hectare; with application before emergence of the plants and for the treatment of existing crops they are preferably up to 4 kg per hectare.

Some of the active substances of the invention further exhibit, pronounced to a greater or lesser degree, the property of translocation, which is of value for the control of weeds: Applied in a test on young soya plants to the upper leaves, these active substances migrate in the sap stream of the plant (phloem) downwards and not only cause the upper parts to die off by contact action but prevent also the sprouting of new axillary buds, or effect the dying off of existing axillary buds, on the branchings of the lower sections of the stems. This property opens up interesting aspects for the control of perennial weeds, particularly if, as a result of translocation, there can be achieved a migration of active substance from the leaves down to the roots.

The compositions of the invention are produced in a manner known per se by the intimate mixing and grinding of active substances of the formula I with suitable carriers, optionally with the addition of dispersing agents or solvents that are inert to the active substances. The active substances can be obtained and used in the following forms:
solid preparations: dusts, scattering agents, granulates (coated granulates, impregnated granulates and homogeneous granulates);
water-dispersible active-substance concentrates: wettable powders, pastes and emulsions;
liquid preparations: solutions.

The solid preparations (dusts, scattering agents and granulates) are produced by the mixing of the active substances with solid carriers. Suitable carriers are, e.g., kaolin, talcum, bole, loess, chalk, limestone, ground limestone, Attaclay, dolomite, diatomaceous earth, precipitated silicic acid, alkaline-earth silicates, sodium and potassium aluminium silicates (feldspars and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Granulates can be produced by dissolving the active substances in an organic solvent, and applying the solution obtained to a granulated mineral, e.g. attapulgite, $SiO_2$, granicalcium or bentonite, and subsequently evaporating off the organic solvent.

Polymer granulates can be produced by impregnating, e.g., a finished porous polymer granulate, such as urea/formaldehyde polymerisates, polyacrylonitrile and polyester, having a specific surface area and a favourable predetermined absorption/desorption ratio, with the active substances, e.g. in the form of their solutions (in a low-boiling) solvent, and removing the solvent. Such polymer granulates can be applied in the form of microgranules having bulk weights of preferably 300 g/liter to 600 g/liter- also by means of sprayers. Spraying can be carried out over extensive areas to be treated by the use of aeroplanes.

Granulates are obtainable also by compacting the carrier material with the active substances and additives, and subsequently crushing the compacted material.

It is possible to add to these mixtures also additives stabilising the active substance, and/or nonionic, anionactive and cation-active substances which improve, e.g., the adhesiveness of the active substances on plants and parts of plants (adhesives and agglutinants), and/or ensure better wettability (wetting agents) as well as dispersibility (dispersing agents). Suitable adhesives are, for example, olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 atoms in the alkyl radical, ligninsulphonic acid, the alkali metal salts and alkalineearth metal salts thereof, polyethylene glycol ethers (carbowaxes), fatty alcohol polyglycol ethers having 5 to 20 ethylene oxide radicals per molcule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e. wettable powders, pastes and emulsion concentrates, are agents which can be diluted with water to give any desired concentration. They consist of active substance, carrier, optionally additives stabilising the active substance, surface-active substances, and antifoaming agents and, optionally, solvents.

The wettable powders and pastes are obtained by the mixing and grinding of the active substances with dispersing agents and pulverulent carriers, in suitable devices, until homogeneity is obtained. Suitale carriers are, e.g., those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali metal salts, ammonium salts and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols or heptadecanols, and salts of sulphated fatty alcohol polyethylene glycol ethers, the sodium salt of oleyl methyl tauride, ditertiary acetylene glycols, dialkyl dilauryl ammonium chloride, and fatty acid alkali-metal and alkaline-earth metal salts.

Suitable anti-foaming agents are, e.g., silicones.

The active substances are so mixed, ground, sieved and strained with the above-mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g., alcohols, benzene, xylenes, toluene, dimethylsulphoxide, N,N-dialkylated amides and trialkylamines. The solents must be practically odourless, nonphytotoxic, inert to the active substances and not readily combustible.

Furthermore, the compositions according to the invention can be used in the form of solutions. For this purpose, the active substance, or several active substances, of the general formula I is, or are, dissolved in suitable organic solvents, solvent mixtures, water, or mixtures of organic solvents with water. As organic solvents, it is possible to use aliphatic and aromatic hydrocarbons, their chlorinated derivatives and alkylnaphthalenes, singly or in admixture with each other.

Other biocidal active substances or agents can be mixed with the described compositions of the invention. For the broadening of their shpere of action, the new compositions can for example contain, in addition to the stated compound of the general formula I, insecticides, fungicides, bactericides, fungistatics, bacteriostatics, or nematocides. The compositions of the invention may also contain fertilisers, trace elements, etc..

The content of active substance in the above described compositions is between 0.1 and 95%, preferably between 1 to 80%. Preparations to be applied can be diluted down to 0.001%. The amounts applied are as a rule between 0.1 and 10 kg of active substance per hectare, preferably between 0.25 and 5 kg of active substance per hectare. The active substances of the formula I can be formulated, for example, as follows (parts denote parts by weight):

Dusts:

The following substances are used to produce a) a 5% dust and b) a 2% dust:
   a. 5 parts of 1-(3,5-bis-trifluoromethylphenyl)-2-oxo-pyrrolidine-4-carboxylic acid, 95 parts of talcum;
   b. 2 parts of the sodium salt of 1-(3,5-bis-trifluoromethylphenyl)-2-oxo-pyrrolidine-4-carboxylic acid, 1 part of highly dispersed silicic acid, 97 parts of talcum.

The active substances are mixed and ground with the carriers.

Granulate:

The following substances are used to produce a 5% granulate:
   5 parts of 1-(3,5-bis-trifluoromethylphenyl)-2-oxopyrrolidine-4-carboxylic acid methyl ester,
   0.25 of epichlorohydrin,
   0.25 part of cetyl polyethylene glycol ether having 8 moles of ethylene oxide,
   3.50 parts of polyethylene glycol, 91 parts of kaolin (particle size 0.3 to 0.8 mm).

The active substance is mixed with epichlorohydrin and dissolved with 6 parts of acetone; the polyethylene glycol and cetyl polyethylene glycol ether are then added. The solution thus obtained is sprayed onto kaolin, and the acetone is subsequently evaporated off.

Wettable powders:

The following constituents are used to produce a) a 50%, b) a 25 and c) a 10% wettable powder:
   a. 50 parts of the sodium salt of 1-(3,5-bis-trifluoromethylphenyl)-2-oxo-pyrrolidine-4-caboxylic acid, 5 parts of sodium dibutyl-naphthalene sulphonate, 3 parts of naphthalenesulphonic acid/phenolsulphonic acid/formaldehyde condensate 3:2:1, 20 parts of kaolin, 22 parts of Champagne chalk;
   b. parts of 1-(3,5-bis-trifluoromethylphenyl)-2-oxopyrrolidine-4-carboxylic acid-N,N-dimethylamide, 5 parts of the sodium salt of oleylmethyl tauride, 2.5 parts of naphthalenesulphonic acid/- formaldehyde condensate, 0.5 parts of carboxymethylcellulose, 5 parts of neutral potassium aluminium silicate, 62 parts of kaolin;

c. 10 parts of 1-(3,5-bis-trifluoromethylphenyl)-2-oxopyrrolidine-4-carboxylic acid-β-butyloxyethyl ester, 3 parts of a mixture of the sodium salts of saturated fatty alcohol sulphates, 5 parts of naphthalenesulphonic acid/formaldehyde condensate, 82 parts of kaolin.

The given active substance is absorbed onto the appropriate carriers (kaolin and chalk), and the whole is subsequently mixed together and ground. There are obtained wettable powders having excellent wettability and suspension properties. From such wettable powders there can be obtained, by dilution with water, suspensions having any desired concentration of active substance. Such suspensions are used for the control of weeds and wild grasses in cultivated crops in the pre-germination (pre-emergence) process and for the treatment of lawns.

Paste:

The following substances are used for producing a 45% paste:

45 parts of 1-(3,5-bis-trifluoromethylphenyl)-2-oxo-pyrrolidine-4-carboxylic acid-N-n-propylamide,
5 parts of sodium aluminum silicate,
14 parts of cetylpolyethylene glycol ether having 8 moles of ethylene oxide,
1 part of oleylpolyethylene glycol ether having 5 moles of ethylene oxide,
2 parts of spindle oil,
23 parts of water,
10 parts of polyethylene glycol.

The active substance is intimately mixed and ground in devices suitable for the purpose. There is obtained a paste from which there can be obtained, by dilution with water, suspensions of any desired concentration. The suspensions are suitable for the treatment of lawns.

Emulsion concentrate

The following constituents are mixed together to produce a 25% emulsion concentrate:

25 parts of 1-(3,5-bis-trifluoromethylphenyl)-2-oxo-pyrrolidine-4-carboxylic acid allyl ester,
5 parts of a mixture of nonylphenolpolyoxyethylene and calcium-dodecylbenzene-sulphonate,
35 parts of 3,5,5-trimethyl-2-cyclohexen-1-one,
35 parts of dimethylformamide.

This concentrate can be diluted with water to give emulsions of suitable concentration.

Instead of employing the particular active substance given in each of the preceding formulation examples, it is also possible to use any other of the compounds embraced by the formula I.

The effectiveness of compounds of the formula I according to the invention has been tested as follows:

I. Inhibition of the growth of grasses in a greenhouse

The grasses
Lolium perenne,
Poa pratensis,
Festuca ovina and
Dactylis glomerata are sown, in a greenhouse, in plastics trays containing a soil/peat/sand mixture. Three weeks after emergence, the grasses are cut back to a height of 4 cm above the soil, and two days thereafter are sprayed with aqueous preparations of the active substances listed below. Converted, the amount of active substance represents 5 kg of active substance per hectare. A tray sown with grass which had not been treated serves in each case as the control speciman. The rate of growth of the grasses is examined three weeks after application of the active substances. Active substances employed:

1-(3,5-bis-trifluoromethylphenyl)-2-oxo-pyrrolidine-4-carboxylic acid methyl ester,
1-(3,5-bis-trifluoromethylphenyl)-2-oxo-pyrrolidine-4-carboxylic acid,
sodium salt of 1-(3,5-bis-trifluoromethylphenyl)-2-oxo-pyrrolidine-4-carboxylic acid, as well as the compounds of the Examples 4, 6, 10, 19, 26, 49 and 63.

In the above test, the stated compounds of the invention produce in the case of all grasses an intense to very pronounced inhibition of growth. The grasses treated with comparable, hitherto known compounds according to U.S. Patent Specification No. 3,136,620 exhibit no, or only slight, inhibition of growth.

II. Inhibition of growth of cereals

Spring wheat "Svenno" (Triticum aestivum) and Spring barley "Herta" (Hordeum vulgare) are sown, in a greenhouse, in plastics pots containing sterilised standard soil. The plants are sprayed one week after emergence with aqueous preparations of the active substances given in Test I. Converted, the amounts of active substance correspond to 6 kg of active substance per hectare or 2 kg of active substance per hectare. Untreated plants are used as control specimens. The rate of growth of the cereal plants is determined three weeks after application of the active substances.

Compared with the untreated control plants, the cereal plants treated with the active substances of the invention display in this test a more intense green colouration. The compounds of the invention, such as the compounds of, inter alia, the Examples 1, 2, 3, 4, 6, 19, 49 and 63 moreover produce the desired inhibition of the growth of internodes. The cereal plants treated with the prior known compounds according to the U.S. Pat. No. 3,136,620 exhibited no, or only very slight, inhibition of growth.

III. Vegetative inhibition of growth and increase of yield of soya beans

Soya beans of the variety "Grosskern" are sown, in a greenhouse, in plastics pots containing a soil/peat/sand mixture. Two weeks after emergence, the plants are sprayed, until dripping off commences, with aqueous preparations of the active substances given in Test I. The concentration of active substance in the spray liquor is in the one case 500 ppm and in the other case 100 ppm. Untreated plants are used as control specimens. The rate of growth of the soya plants is determined three weeks after application of the active substances.

Compared with the control plants, the plants treated with the active substances of the invention display a more intense green colouration. Furthermore, it is shown that there has occurred a medium to extensive inhibition of growth, e.g. with the compound of the Example 1. Prior known active substances according to U.S. Pat. Specification No. 3,136,620 cause in some cases serious leaf damage and/or produce no, or only slight, inhibition of growth.

IV. Inhibition of growth on an outdoor lawn

An established lawn in the open, consisting of 20% of Lolium perenne, 25% of Poa pratensis, 45% of Festuca rubra and 10% of Agrostis tenuis, is used as a test area. With a height of growth of 9 cm, after the first cut in the spring, plots of 3 square meters in area are uniformly sprayed with aqueous preparations of the active substances given in the following. The amounts applied are equivalent respectively to 5 kg of active substance per hectare (AS/hectare). Untreated plots of the same size as well as strips between the individual plots are used as control areas.

The mean height in growth of the grasses aboveground in the treated and untreated plots is measured 1, 4 and 12 weeks after application of the active substances. The results are given in the following Table.

| Treatment/active substance | Mean growth in height of the grasses above-ground | | |
|---|---|---|---|
| | 1 week after application | 4 weeks after application | 12 weeks after application |
| 1-(3,5-bis-chloro-phenyl)-2-oxo-pyrrolidine-4-carboxylic acid | | | |
| 5 kg of AS/hect. | 12 cm | 21 cm | 58 cm |
| 2.5 kg of AS/hect. | 12 cm | 24 cm | 61 cm |
| 1-3(3,5-bis-trifluoro-methylphenyl)-2-oxo-pyrrolidine-4-carboxylic acid methyl ester | | | |
| 5 kg of AS/hect. | 10 cm | 12 cm | 17 cm |
| 2.5 kg of AS/hect. | 12 cm | 14 cm | 26 cm |
| untreated | 12 cm | 23 cm | 59 cm |

V. Inhibition of side shoots on tobacco plants

Eight weeks after sowing, tobacco Nicotiana tabacum (variety Xanthi) are transplanted to pots in a greenhouse, normally watered and treated weekly with nutrient solution. Two weeks after potting, there are chosen per treatment three plants; of these plants one remains untopped and from the two others the growth tip is removed five days before treatment.

Per plant there is then sprayed, laterally from above onto the leading shoot and the upper leaf axils, 10 ml of liquor containing active substance (concentrations: 2.6; 1.3 and 0.6% corresponding to 6.3 and 1.5 kg per hectare in the open). A part of the liquor consequently runs down the petioles and into the remaining lower leaf axils (contact with side-shoot buds).

After setting up of the tests in the greenhouse and watering, the tests are evaluated 4 and 14 days after application of the test liquor.

Contact effect and systemic effect are evaluated separately.
Contact effect: Assessment of the 6 uppermost side shoots:
9 = side shoots as in the case of untreated control plant,
5 = about 50% damage on side shoots,
1 = side shoots completely destroyed.
Systemic effect: Assessment of the uppermost side shoots.
Same scale of values (5 = 50% inhibition of growth without contact effect),
1 = complete inhibition of growth; contact-effect value 1 excludes sytemic effect.

Excellent results are obtained in these tests with the active substances of the invention, such as in particular with those of, inter alia, the Example 1, 2, 3, 6, 10, 19, 25 and 26.

VI. Action in breadth on monocotyledonous and dicotyledonous weeds in selected useful crops Immediately after sowing of the test plants in seed trays, the active substances are applied as an aqueous suspension, obtained from a 25% wettable powder, at two different concentrations (4 and 2 kg/hectare) to the surface of the soil. The seed trays are then kept at 22° – 23° C with 50 to 70% relative humidity. The test results are evaluated after 28 days. The following test plants are used:

Weeds
  Avena fatua, Alopecurus myosuorides, Cyperus esculentus, Setaria italica, Echinochloa crus galli, Sesbania exaltata, Amarantus retroflexus, Chrysanthemum leuc. Sinapis alba, Ipomoea purpurea, Pastinaca sativa.

Cultivated plants
  maize (Zea maize), cotton (Gossypium herbaccara).

The active substances of the invention have in this test an excellent action on the given test weeds.

VII. Herbicidal action of the active substances after emergence of the plants (post-emergence application).

The test plants are treated in the 2–4-leaf stage, about 10 days after sowing, with aqueous suspensions of the active substances, obtained from 25% wettable powders. After the treatment, the plants are maintained at 22°–25° C with 50 to 70% relative humidity in a greenhouse.

The following are used as test plants:
Weeds: Avena fatua, Alopecurus myosuorides, Cyperus esculentus, Echinochloa crus galli, Sesbania exaltata, Sinapis alba.

Cultivated plants: maize (Zea maize), Sorghum hybridum, dry rice (Oryza), cotton (Gossypium herbaccara), lucerne (Medicago sativa).

The test results are evaluated after 15 days. It is shown that the compounds of the invention, particularly 1-(3,5-bis-trifluoromethylphenyl)-2-oxo-pyrrolidine-4-carboxylic acid methyl ester, have a very good herbicidal action when applied in the usual amounts of 2 to 4 kg of active substance per hectare, with negligible damage being suffered by the cultivated plants.

We claim:
1. A 1-(bis-trifluoromethylphenyl)-2-oxo-pyrrolidine-4-carboxylic acid derivative of the formula I

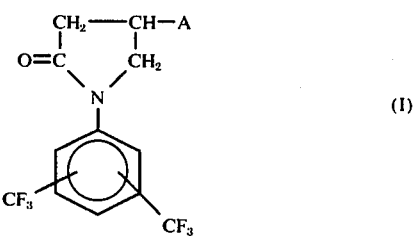

wherein
A represents a group —COO⁻ H⁺, —COOR$_1$, —COSR$_2$, —CN, —COCl, —COF,

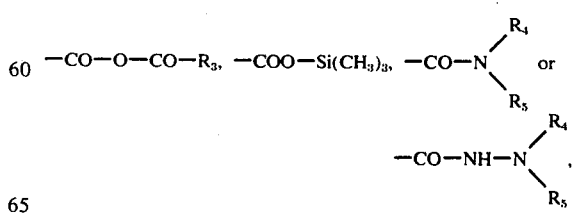

$R_1$ represents a mono- to trivalent metal cation of an inorganic or organic amine cation or quaternary ammonium cation, $C_1$-$C_{18}$-alkyl, $C_1$-$C_{18}$ alkyl substituted by halogen, hydroxyl, $C_1$-$C_4$ alkoxy, $C_1$-$C_4$ alkylthio, amino, mono- or di-($C_1$-$C_4$) alkylamino, cyano, ($C_1$-$C_4$ alk)oxy-carbonyl, carbamoyl, tetrahydrofuryl, tetrahydropyranyl, or oxacyclopropyl; alkenyl, halogenoalkenyl, alkynyl, halogenoalkynyl having 3 to 8 carbon atoms, cycloalkyl having 3 to 12 ring carbon atoms, phenyl, benzyl, phenethyl, or phenyl, benzyl or phenethyl substituted by $C_1$-$C_4$ alkyl, $C_1$-$C_4$ alkoxy, $C_1$-$C_4$ alkylthio, N-($C_1$-$C_4$ alkyl) amino, N, N-($C_1$-$C_4$) dialkylamino, halogen, trifluoromethyl, amino or nitro, $R_2$ represents alkyl having 1 to 6 carbon atoms, phenyl, benzyl, or phenyl or benzyl substituted by $C_1$-$C_4$ alkyl, $C_1$-$C_4$ alkoxy, $C_1$-$C_4$ alkylthio, N-($C_1$-$C_4$ alkyl) amino, N, N-($C_1$-$C_4$) dialkylamino, halogen, trifluoromethyl, amino or nitro, $R_3$ represents $C_1$-$C_4$-alkyl, $C_1$-$C_4$ alkyl substituted by at most 3 halogen atoms, or phenyl, $R_4$ and $R_5$ each independently represent hydrogen, $C_1$-$C_6$ alkyl, $C_1$-$C_6$ alkyl substituted by halogen, hydroxyl, $C_1$-$C_4$ alkoxy, $C_1$-$C_4$ alkylthio, amino, mono- or di-($C_1$-$C_4$)alkylamino, cyano, ($C_1$-$C_4$ alk)oxy-carbonyl, carbamoyl, tetrahydrofuryl, tetrahydropyranyl, or oxacyclopropyl; $C_3$-$C_8$-alkenyl, cycloalkyl having 3 to 8 ring carbon atoms, phenyl, phenyl substituted by $C_1$-$C_4$ alkyl, $C_1$-$C_4$ alkoxy, $C_1$-$C_4$ alkylthio, N-($C_1$-$C_4$ alkyl) amino, N, N-($C_1$-$C_4$) dialkylamino, halogen, trifluoromethyl, amino or nitro, or $R_4$ and $R_5$ together with the adjacent nitrogen atom also represent a saturated 3- to 8-membered heterocyclic ring, and said ring substituted by $C_1$-$C_4$ alkyl.

2. The 1-(Bis-trifluoromethylphenyl)-2-oxo-pyrrolidine-4carboxylic acid derivative according to claim 1 wherein the two $CF_3$-groups in the formula I are in the 3- and 5-position of the phenyl radical.

3. The carboxylic acid derivative according to claim 1 wherein A represents the -COOH group or a group -COOR$_1$ or -COSR$_2$, wherein $R_1$ and $R_2$ are as defined in claim 1.

4. As carboxylic acid derivative according to claim 1, the compound 1-(3,5-bis-trifluoromethylphenyl)-2-oxo-pyrrolidine-4-carboxylic acid and the sodium salt thereof.

5. As carboxylic acid derivatives according to claim 1, the lower alkyl esters of 1-(3,5-bis-trifluoromethylphenyl)-2-oxo-pyrrolidine-4-carboxylic acid.

6. As carboxylic acid derivative according to claim 1, the tetrahydrofurfuryl ester of 1-(3,5-bis-trifluoromethylphenyl)-2-oxy-pyrrolidine-carboxylic-acid.

7. Plant-growth-regulating composition containing as active substance an effective amount of a carboxylic acid derivative of the formula I of claim 1, together with a suitable carrier therefor.

8. Method for the regulation of plant growth, such as the inhibition of the growth or grasses and cereals, reduction of side shoots on tobacco plants, increase of the yield of soya beans, and the abscission of fruit, which comprises applying to the plant an effective amount of a pyrrolidine carboxylic acid derivative of the formula I of claim 1.

* * * * *